US006440695B1

(12) United States Patent
Merryman et al.

(10) Patent No.: US 6,440,695 B1
(45) Date of Patent: *Aug. 27, 2002

(54) METHOD FOR PRODUCING DIVERSE LIBRARIES OF ENCODED POLYPEPTIDES

(75) Inventors: Charles Everett Merryman, Beverly Farms; David P. Bartel, Brookline, both of MA (US)

(73) Assignee: Whitehead Institute for Biomedical Research, Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/291,704

(22) Filed: Apr. 14, 1999

Related U.S. Application Data (60) Provisional application No. 60/082,252, filed on Apr. 17, 1998.

(51) Int. Cl.⁷ .................................. C12P 21/06
(52) U.S. Cl. ....................... 435/69.1; 435/69.7
(58) Field of Search .................. 435/6, 68.1, 69.1, 435/69.7; 536/25.3; 530/322

(56) References Cited

U.S. PATENT DOCUMENTS

| | | | |
|---|---|---|---|
| 5,616,459 A | * | 4/1997 | Kramer et al. |
| 5,658,754 A | * | 8/1997 | Kawasaki et al. |
| 5,756,330 A | * | 5/1998 | Lawlor |
| 5,837,844 A | * | 11/1998 | Hsu |
| 5,843,701 A | * | 12/1998 | Gold |
| 5,922,545 A | | 7/1999 | Mattheakis et al. ............ 435/6 |
| 6,077,993 A | * | 7/1999 | Mahajan |
| 6,143,503 A | * | 11/2000 | Baskerville et al. ........... 435/6 |
| 6,194,550 B1 | | 2/2001 | Gold et al. .................. 530/358 |
| 6,207,446 B1 | | 3/2001 | Szostak et al. .......... 435/287.2 |

FOREIGN PATENT DOCUMENTS

WO   WO 98/55652 A1   12/1998

OTHER PUBLICATIONS

Matzke, A.J., et al., "Mechanism of translocation: relative arrangement of tRNA and mRNA on the ribosome," *Proc. Natl. Acad. Sci. USA* 77 (9):5110–4 (Sep. 1980).

Greenberg, J.R., "Proteins crosslinked to messenger RNA by irradiating polyribosomes with ultraviolet light," *Nucleic Acids Res.* 8 (23):5685–701 (Dec. 11, 1980).

Schimmel P.R., et al., "Photo–cross–linking of protein–nucleic acid complexes," *Methods Enzmol*, 46:168–80 (1977).

Semenkov, Y. et al., "Puromycin reaction for the A sitebound peptidyl–tRNA" *FEBS Lett* 296 (2): 207–10 (Jan. 20, 1992).

Roesser, J.R., et al., "Ribosome–catalyzed formation of an abnormal peptide analogue" *Biochemistry* 25 (21):6361–5 (Oct. 21, 1986).

Katunin, V., "Effect of the nucleotide–37 on the interaction of tRNA (Phe) with the P site of Escherichia coli ribosomes," *Biochimie* 76 (1):51–7 (1994).

Nishikawa, K. et al., "A structurally modified yeast tRNA$^{Phe}$ with six nucleotides in the anticoden loop lacks significant phenylalanine acceptance," *J. Biol. Chem.* 257 (18):10536–9 (Sep. 25, 1982).

Mattheakis, L.C., et al., "An in vitro polysome display system for identifying ligands from very large peptide libraries" *Proc. Natl. Acad. Sci. USA* 91(19):9022–6 (Sep. 13, 1994).

Matteakis, L.C., et al., "Cell–free synthesis of peptide libraries displayed on polysomes" *Methods Enzymol* 267:195–207 (1996).

Lebl M., et al., "Synthetic peptide libraries" *Methods Enzymol* 289:336–92 (1997).

Matzke, A. J., et al., "Photo–induced crosslinking between phenylalanine transfer RNA and messenger RNA on the Escherichia coli ribosome" *Eur. J. Biochem.* 112 (1):169–78 (Nov. 1980).

Steiner, G. et al., "Crosslinking transfer RNA and messenger RNA at the ribosomal decoding region: identification of the site of reaction on the messenger RNA," *Nucleic Acids Res* 12(21):8181–91 (Nov. 1984).

Hanes, J., et al., "In vitro selection and evolution of funcational proteins by using ribosome display" *Proc. Natl. Acad. Sci. USA* 94:4937–4942 (1997).

Favre, A., et al., "Thionucleobases as intrinsic photoaffinity probes of nucleic acid structures and nuclei acid–protein interactions," *J. Photochem Photobiol B.* 42 (2) :109–24 (Feb. 1998).

Nemoto, N., et al., "In vitro virus: Bonding of mRNA bearing puromycin at the 3'–terminal end to the C–terminal end of its encoded protein on the ribosome in vitro," *FEBS Lett* 414 (2) :405–408 (Sep. 1997.

Roberts, R.W. and Szostak, J.W., "RNA–peptide fusions for the *in vitro* selection of peptides and proteins," *Proc. Natl. Acad. Sci. USA* 994 (23):12297–12302 (Nov. 1997).

Godard G., et al., "Photochemically and chemically activatable antisense oligonucleotides: comparision of their reactivities towards DNA and RNA targets," *Nucleic Acids Res.* 22 (22):4789–4795 (Nov. 1994.

Sprinzl, M., et al., "Enzymatic incorporation of ATP and CTP analogues into the 3' end of tRNA," *Eur. J. Biochem.* 81(3): 579–589 (Dec. 1977).

Fraser, T.H. and Rich, A., "Synthesis and aminoacylation of 3'–amino–3'–deoxy transfer RNA and its activity in ribosomal protein synthesis," Proc. Natl. Acad. Sci. USA, 70 (9):2671–5 (Sep. 1973).

* cited by examiner

*Primary Examiner*—Ralph Gitomer
(74) *Attorney, Agent, or Firm*—Hamilton, Brook, Smith & Reynolds, P.C.

(57) ABSTRACT tRNA analogues which comprise a tRNA, such as tRNA$^{Phe}$; an amino acid moiety which acts as an acceptor substrate, but not as a donor substrate, for ribosome-directed peptidyl transfer and, thus, is stably linked to the acceptor stem of the tRNA; and a reactive or activatible moiety near or within the anticodon stem loop of the tRNA that can medidate the covalent coupling of the tRNA analogue to mRNA. Also described are polypeptide-tRNA analogue-mRNA fusions; libraries of encoded polypeptides; methods of producing and screening the libraries; and target members and their uses.

11 Claims, 3 Drawing Sheets

Fig 2

SEQUENCE LISTING

```
<160> NUMBER OF SEQ ID NOS: 4

<210> SEQ ID NO 1
<211> LENGTH: 36
<212> TYPE: DNA
<213> ORGANISM: Artificial Sequence
<220> FEATURE:
<223> OTHER INFORMATION: Primer for E. Coli Chromosomal DNA

<400> SEQUENCE: 1
taatacgact cactataggc tacgtagctc agttgg                              36

<210> SEQ ID NO 2
<211> LENGTH: 20
<212> TYPE: DNA
<213> ORGANISM: Artificial Sequence
<220> FEATURE:
<223> OTHER INFORMATION: Primer for E. Coli Chromosonal DNA

<400> SEQUENCE: 2
tggtggctac gacgggattc                                                20

<210> SEQ ID NO 3
<211> LENGTH: 34
<212> TYPE: DNA
<213> ORGANISM: Artificial Sequence
<220> FEATURE:
<223> OTHER INFORMATION: + Strand Primer

<400> SEQUENCE: 3
taatacgact cactataggt aaagtgtcat tagc                                34

<210> SEQ ID NO 4
<211> LENGTH: 22
<212> TYPE: DNA
<213> ORGANISM: Artificial Sequence
<220> FEATURE:
<223> OTHER INFORMATION: - Strand Primer

<400> SEQUENCE: 4
ctttatcttc agaagaaaaa cc                                             22
```

METHOD FOR PRODUCING DIVERSE LIBRARIES OF ENCODED POLYPEPTIDES

RELATED APPLICATION

This application claims the benefit of U.S. provisional application 60/082,252, entitled "Method for producing Diverse Libraries of Encoded Peptides," by Charles E. Merryman and David P. Bartel, filed Apr. 17, 1998. The entire teachings of the referenced provisional application are incorporated herein by reference.

BACKGROUND OF THE INVENTION

Large combinatorial libraries of biopolymers are starting points for isolating new enzymes, binding motifs and other useful molecules. For example, current technologies can generate populations of nucleic acids with complexities on the order of $10^{15}$ molecules and then isolate and identify a single molecule with a desired activity. Random polypeptide populations have greater chemical diversity than do polynucleotides, making them an attractive alternative to nucleic acids. Current systems are limited in their ability to easily generate large complex libraries of polypeptides that are in a form that allows the isolation and identification of rare molecules with a desired activity.

SUMMARY OF THE INVENTION

The present invention relates to tRNA analogues; polypeptide-tRNA-analogue-mRNA fusions; diverse libraries of encoded polypeptides; and a method of producing the diverse libraries. tRNA analogues of the present invention comprise a tRNA (such as a yeast tRNA); an amino acid moiety that acts as an acceptor substrate, but not as a donor substrate, for ribosome-directed peptidyl transfer; and a reactive or activatible moiety near or within the anticodon stemp loop of the tRNA that can mediate the stable coupling of the tRNA analogue to mRNA. An amino acid moiety is stably linked to the tRNA if the linkage between the two or the chemical environment allows the amino acid moiety to act as an acceptor substrate but not as a donor substrate for ribosome-directed peptidyl transfer. In a specific embodiment, the tRNA analogue is a 3'-amino-3'-deoxyadenosine-substituted tRNA in which the 3'-terminal A of yeast tRNA$^{phe}$ is replaced or substituted by 3'-amino-3'-deoxyadenosine and then the substituted tRNA is charged with phenylalaine. This tRNA analogue is termed PHE-N-tRNA. In another specific embodiment, the tRNA analogue is a puromycin-substituted tRNA in which the 3'-terminal A of yeast tRNA$^{phe}$ is replaced or substituted by puromycin, with the result that the amino acid moiety is the methoxytyrosine moiety of puromycin. In both embodiments, the reactive or activatible moiety near or within the anticodon stem-loop is the modified Y base of yeast tRNA$^{phe}$.

Also the subject of this invention are polypeptide-tRNA analogue-mRNA fusions, in which: the polypeptide can be a peptide or polypeptide of any size; the tRNA analogue is as described herein; and the mRNA is mRNA which encodes the polypeptide component of the fusion. In a fusion, the tRNA analogue component is: (a) located between the polypeptide and the mRNA which encodes the polypeptide; (b) linked to the polypeptide by a stable bond between the terminal amino acid residue of the polypeptide and the amino acid moiety of the tRNA analogue; and (c) linked to the mRNA by crosslinks between a reactive or activatible moiety of the tRNA analogue and the mRNA. In one embodiment, the polypeptide-tRNA analogue-mRNA fusion includes a PHE-N-tRNA (and, thus, the amino acid moiety which acts as an acceptor substrate but cannot act as a donor substrate is phenylalanine) and the tRNA is yeast tRNA$^{phe}$. In another embodiment, the polypeptide-tRNA analogue-mRNA fusion includes a puromycin-substituted tRNA (and, thus, the amino acid moiety which acts as an acceptor substrate but cannot act as a donor substrate is the methoxytyrosine moiety of puromycin) and the tRNA is yeast tRNA$^{phe}$.

Diverse libraries or collections of encoded polypeptides are also the subject of this invention. A diverse library or collection comprises the encoded polypeptides, which are the polypeptide-tRNA analogue-mRNA fusions described herein. Methods of producing such libraries are also the subject of this invention.

The invention further relates to a method of screening a diverse encoded polypeptide library to identify target members (library members with desired biological or biochemical properties or activities, such as binding to a particular ligand or enzymatic activity). In one embodiment of screening a diverse encoded polypeptide library to identify a target member or members, the diverse library is initially enriched in molecules with desired properties. This is done, for example, to identify a binding partner or ligand of interest using known enrichment methods, such as affinity enrichment using an immobilized ligand or binding partner or to identify a library member with enzymatic activity by assessing affinity of a library member to a product of a reaction in which the enzyme has modified itself or a substrate to which the library member is attached. Library members identified in this way are target members. In a further step in the method, a library which has been enriched in target members (an enriched fusion or encoded diverse polypeptide library) is amplified and subjected to additional enrichment. For example, the enriched library is reverse transcribed, thereby producing cDNAs of the mRNA components; the cDNAs are, optionally, amplified. The initially produced cDNAs or the resulting PCR products are subjected to in vitro transcription, thereby producing an amplified pool of mRNAs that encode members of the enriched fusion library. The amplified pool of mRNAs is subjected to in vitro translation in the presence of the tRNA analogue of the present invention, producing an amplified versionof the enriched encoded polypeptide library. Library members (fusions) amplified in this manner are, optionally, subjected to further enrichment and amplification, as necessary, until target members are enriched to a level where they are present in sufficient numbers to be detected. They are detected using any known method, such as binding to a ligand of interest or catalyzing a reaction of interest. mRNAs of target members are cloned and then individual fusions made from cloned mRNAs are screened for the desired properties (e.g., by ligand binding or catalyzing a reaction of interest). Library members identified in this way are target members, which are also a subject of this invention.

Target members are polypeptide-tRNA analogue-mRNA fusions. The translation products of the enriched mRNA (the polypeptide component of a target member) which display properties of interest and modified or engineered derivatives of the translation products which display properties of interest are target polypeptide fragments. These fragments are also a subject of this invention. As used herein, the term target polypeptide fragments includes fragments released or separated from target members in which they occur and fragments produced or synthesized by another method (e.g., chemical synthesis, mRNA translation in the absence of the tRNA analogue or a recombinant DNA method in which DNA encoding a desired target polypeptide fragment is expressed). Target polypeptide fragments include, but are not limited to, protein catalysts, single-chain monoclonal antibodies, binding pair members (ligand or binding partner), receptors or their ligands, and enzymes and their substrates.

DETAILED DESCRIPTION OF THE INVENTION

The present invention relates to a modified tRNA or functional analogue of tRNA (both referred to herein as a tRNA analogue) that comprises 1) a tRNA or tRNA-like molecule; 2) an amino acid moiety, which is an amino acid, a modified amino acid, or other amino-acid like molecule that can act as an acceptor substrate for ribosome directed peptidyl transfer, but cannot act as a donor substrate for ribosome-directed peptidyl transfer; thus, it is stably linked to the acceptor stem of the tRNA or tRNA-like molecule and 3) a reactive or activatible moiety, which can be any addition, deletion, substitution, modification or alteration of the tRNA (such as addition, deletion, substitution, modification or alteration of one or more bases or nucleotides near or within the anticodon stem-loop of the tRNA), that can mediate the covalent coupling of the tRNA analogue to messenger RNA (mRNA). For example, the activatible moiety can be the naturally occurring modification of guanine (the Y base) that is found in the anticodon loop at position 37 of yeast tRNA$^{phe}$. Such a tRNA analogue is a bifunctional molecule whose amino-acid moiety can accept, but not donate, a polypeptide that is being synthesized (under the direction of the ribosome) and which can specifically link with the mRNA encoding the polypeptide being synthesized. The tRNA analogue can be, for example, a 3'-amino-3'-deoxyadenosine-substituted tRNA or puromycin-substituted tRNA and the amino acid moiety is any amino acid or the methoxytyrosine moiety of a puromycin-substituted tRNA. The tRNA analogue can be, for example, a tRNA in which the 3'terminal nucleotide is replaced by 3'-amino-3'-deoxyadenosine and then linked to an amino acid moiety or replaced by puromycin and in which the anticodon loop comprises a reactive or activatible moiety that can mediate covalent coupling of the tRNA analogue to the mRNA. The tRNA analogue can be used to produce diverse encoded polypeptide libraries, which are also the subject of this invention.

The tRNA analogues can comprise any tRNA or tRNA-like molecule (e.g., bacterial, yeast, mammalian, in vitro transcribed, synthesized, tmRNA, etc.) which: 1) is modified such that the resulting modified tRNA can form a stable link with a polypeptide being expressed and 2) can make a specific link with the mRNA which encodes the polypeptide being expressed (the encoding mRNA). In a specific embodiment, the 3' end of the tRNA is modified such that 3'-amino-3'-deoxyadenosine replaces the A base at the 3' end and then the substituted tRNA is charged with phenylalanine. In another specific embodiment, the 3' end of the tRNA is modified such that puromycin replaces the A base at the 3' end. The tRNA analogue can contain any modification which can form the desired stable peptide-tRNA link. As a result of the formation of a stable peptide-tRNA link, protein synthesis is stalled, presumably after translocation of the peptide-tRNA analogue complex to the P site. The specific link between the tRNA analogue and the mRNA which encodes the polypeptide being produced can be formed by activation of an activatible group or via a reactive group in the tRNA (e.g., the Y base) or mRNA.

In one embodiment, the tRNA analogue is produced by replacing the 3' terminal nucleotide (e.g., the 3' terminal A) of yeast tRNA$^{phe}$ by 3'-amino-3'-deoxyadenosine and charging the tRNA with phenylalanine. In another embodiment, the tRNA analogue is produced by replacing the 3' terminal nucleotide (e.g., the 3' terminal A) of yeast tRNA$^{phe}$ by puromycin. Yeast tRNA$^{phe}$ is useful because it naturally contains a modified guanine base (the Y base) at position 37 that serves as an activatible group that becomes reactive when exposed to UV light, coupling the tRNA analogue to an mRNA. After aminoacylation with phenylalanine, the 3'-amino-3'-deoxyadenosine substitution transforms the yeast tRNA$^{phe}$ into a tRNA analogue (a 3'-amino-3'-deoxyadenosine substituted tRNA) that contains phenylalanine linked to the RNA 3' terminus by an amide bond. In this embodiment, the amino acid moiety is the phenylalanine moiety of the 3'-amino-3'-deoxyadenosine-substituted tRNA. Alternatively, puromycin substitution transforms the yeast tRNA$^{phe}$ into a tRNA analogue (a puromycin-substituted tRNA) that contains methoxytyrosine linked to the RNA 3' terminus by an amide bond. In this embodiment, the amino acid moiety is the methoxytyrosine moiety of the puromycin-substituted tRNA. In both embodiments, the amide linkage between the RNA and the phenylalanine or methoxytyrosine prevents the peptidyl-tRNA analogue from being a suitable donor substrate for ribosome-directed peptidyl transfer and, thus, when a polypeptide is transferred to the amino-acid moiety of the tRNA analogue, the polypeptide becomes stably connected to the tRNA analogue.

Figure 1A:
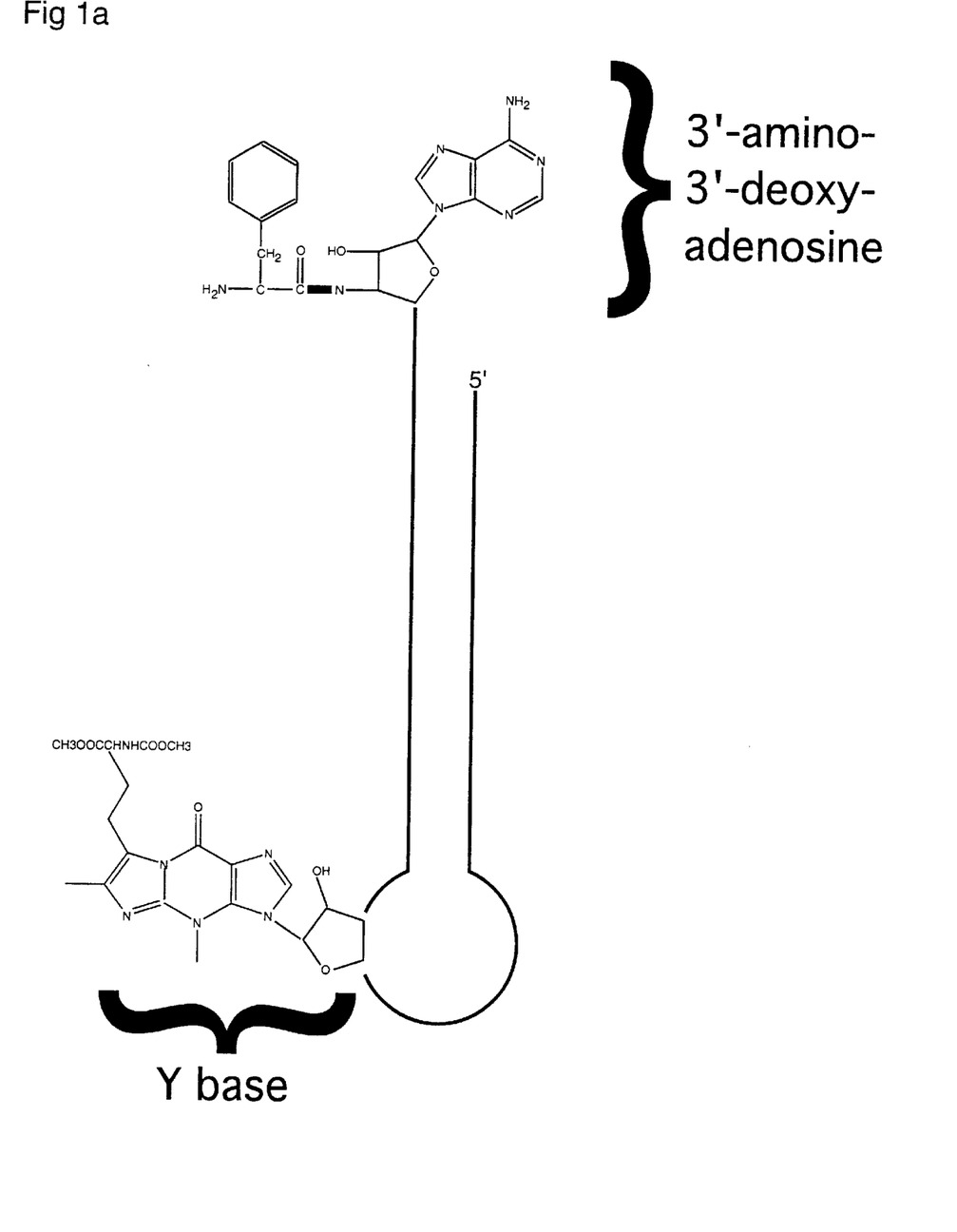
FIGS. 1a and 1b are schematic representations of two embodiments of tRNA analogues of the present invention, in which the tRNA portion is stably linked by an amide bond (very thick line) to the amino acid moiety of the tRNA analogue and the reactive or activatible moiety is a modified nucleotide (Y base) which can be used to couple the tRNA analogue to mRNA when the base is activated by UV irradiation.
Figure 1B:
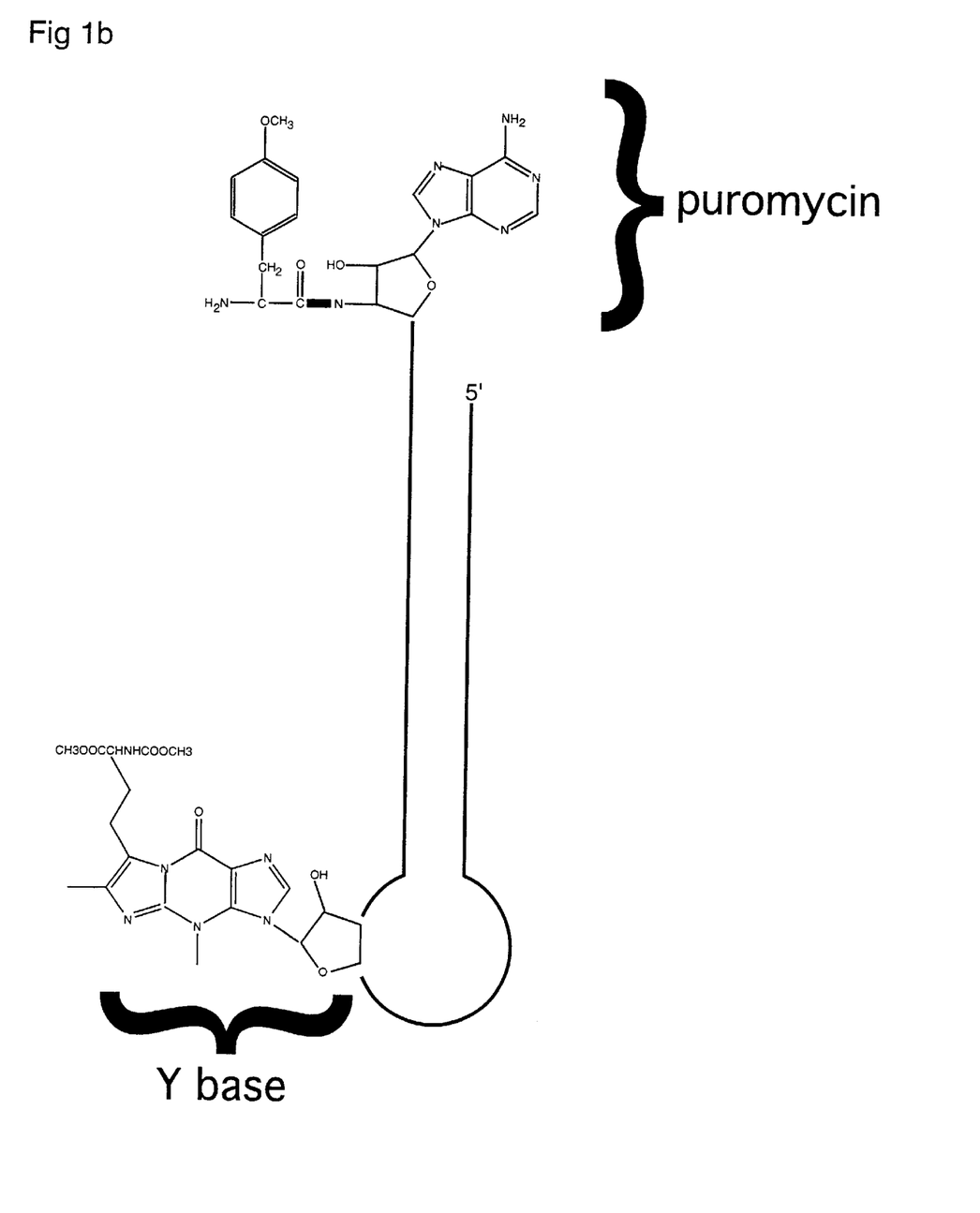
Figure 2:
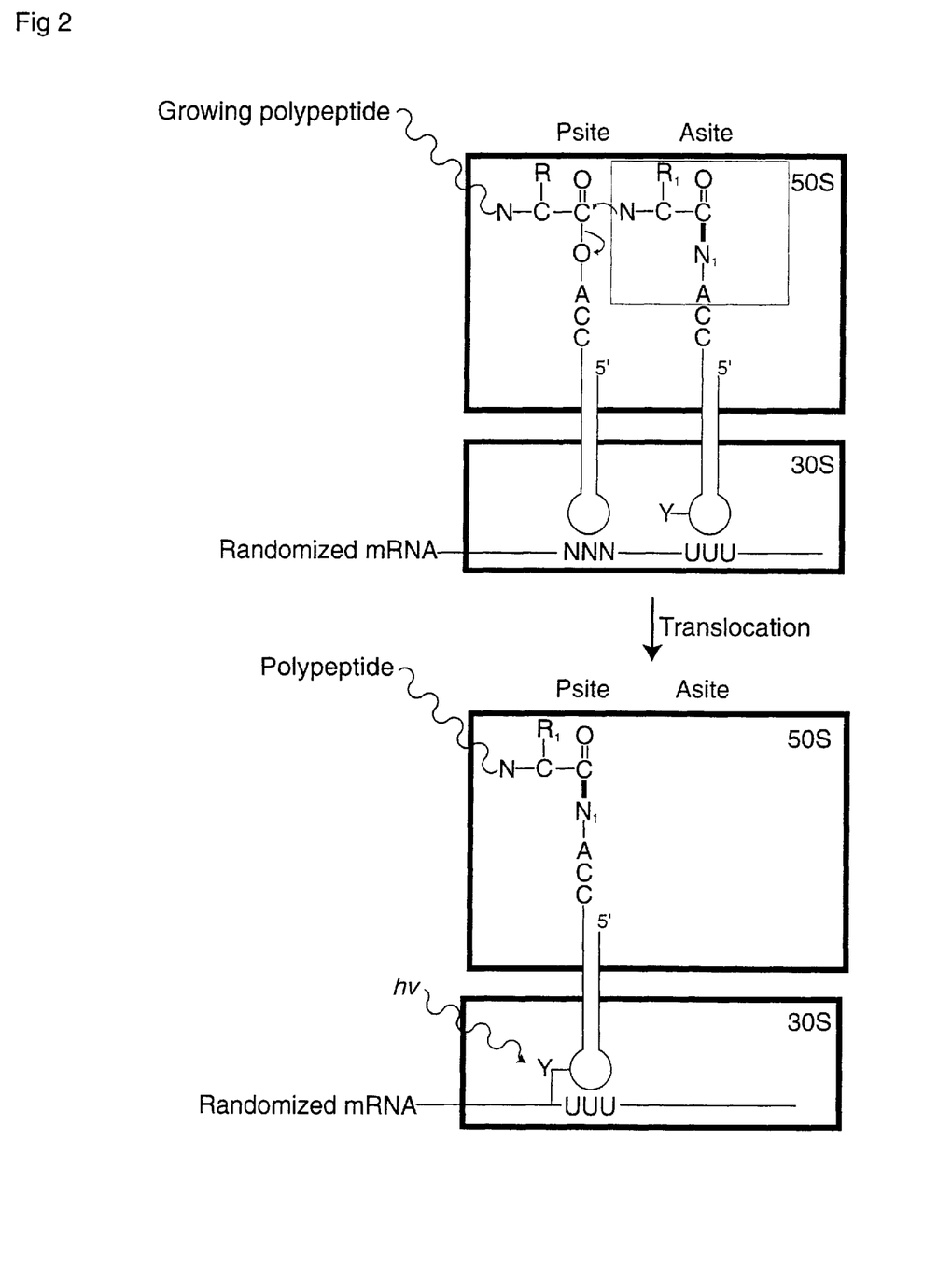
FIG. 2 is a schematic representation of one embodiment of the present invention, in which steps which occur during in vitro translation are presented and the tRNA analogue is a yeast tRNA$^{phe}$ analogue in which the last nucleotide of the acceptor stem has been replaced by 3-amino-3'-deoxyadenosine.

FIGS. 1a and 1b are schematic representations of these embodiments of the present invention. FIGS. 1a and 1b show tRNA analogues that contain an amide bond (very thick line) stably linking the tRNA portion and the amino-acid moiety of the analogue. In FIG. 1a, the tRNA analogue is 3'-amino-3'-deoxyadenosine substituted and the amino acid moiety is a phenylalanine moiety. In FIG. 1b, the tRNA analogue is puromycin substituted and the amino acid moiety is a methoxytyrosine moiety. It also shows the Y base, which is a modified nucleotide which can be used to couple the tRNA analogue to mRNA when the base is activated by UV irradiation. The tRNA portion of the molecule is represented schematically by a thick line. FIG. 2 illustrates the action of the tRNA analogue of this embodiment of the present invention. During translation, when the ribosome reaches a phenylalanine codon (UUU or UUC) in the mRNA, the methoxytyrosine portion (amino-acid moiety) of the tRNA analogue is used as an acceptor substrate and is joined to the carboxy terminus of the nascent polypeptide; because the methoxytyrosine is joined to the tRNA portion of the tRNA analogue by an amide bond, translation stalls. The stalled polypeptide-tRNA$^{phe}$ can be crosslinked to the mRNA (through the Y base of the tRNA$^{phe}$ that was used to make the tRNA analogue) by mild UV irradiation.

The present invention also relates to a diverse library or collection of encoded polypeptides which each comprise three components that are fused into a single molecule that can be produced and manipulated in vitro. Each encoded polypeptide molecule of the library, referred to as a polypeptide-tRNA analogue-mRNA fusion, comprises a polypeptide of any length, an mRNA encoding the polypeptide and a tRNA analogue that is located between the polypeptide and its encoding mRNA and forms a link between these two components. The mRNA component of each fusion can be an mRNA or mRNA-like molecule (of any sequence or length) that is translated by the ribosome. The mRNA component contains elements required for its expression and elements (e.g., primer binding sites) that permit it to be reverse transcribed and then amplified and/or cloned. The tRNA analogue component of each fusion is as described above. That is, the tRNA analogue component, comprises 1) a tRNA or tRNA-like molecule; 2) an amino acid moiety which can act as an acceptor substrate, but not as a donor substrate, for ribosome-directed peptidyl transfer and 3) an activatible moiety that mediates the covalent coupling of the tRNA analogue to messenger RNA.

The diverse library or collection of encoded polypeptides is produced by combining the tRNA analogue with an in vitro translation mixture that contains a diverse mixture of mRNA sequences (such as a randomized pool of mRNAs) and incubating the mixture under conditions appropriate for in vitro translation of mRNA sequences and formation of the linkage between the tRNA analogue and the mRNA. Translation of the mRNAs is stalled as a result of the presence of the stably linked amino acid moiety of the tRNA analogue. At first, members of the diverse collection of mRNAs are translated normally: When a codon is reached, a matching aminoacyl tRNA is selected by the ribosome and bound to the A site. The previously synthesized portion of the nascent polypeptide (which is attached to a P-site bound tRNA) is transferred to the amino acid on the newly selected aminoacyl tRNA (effectively extending the length of the encoded polypeptide by one amino acid) and the tRNA previously bound to the P site is replaced by the newly selected tRNA, which now becomes the P-site bound tRNA. The ribosome uses the now empty A site to match another codon and aminoacyl tRNA. Repetition of this cycle translates mRNA sequences into their corresponding polypeptide sequences. For members of the mRNA of the library this normal translation ends when the tRNA analogue (instead of a normal aminoacyl tRNA) is selected by the ribosome and the ribosome binds the tRNA analogue to the A site. The polypeptide is then transferred to the amino-acid moiety of the tRNA analogue. The stable linkage between the amino-acid moiety and the RNA portion of the tRNA analogue prevents the polypeptide from being further transferred and, thus, translation is stalled with the polypeptide stably attached to the tRNA analogue, which is bound to the mRNA that encodes the polypeptide. Prior to, concurrent with, or after transfer of the polypeptide to the tRNA analogue, the second functionality of the tRNA analogue is used to covalently couple the tRNA analogue to the mRNA. In this way the bifunctional tRNA analogue is used to generate the desired library of polypeptide-tRNA analogue-mRNA fusions.

In one embodiment, the tRNA analogue can be yeast tRNA$^{phe}$, where the 3' terminal nucleotide (e.g., the 3' terminal A of yeast tRNA$^{phe}$) is replaced by 3'-amino-3'-deoxyadenosine and then charged with phenylalanine. In another embodiment, the tRNA analogue can be yeast tRNA$^{phe}$, where the 3' terminal nucleotide (e.g., the 3' terminal A of yeast tRNA$^{phe}$) is replaced by puromycin. The resulting tRNA analogues are bifunctional and during in vitro protein synthesis, they can form a stable link (as a result of ribosome directed peptidyl transfer) with the carboxy-terminal amino acid of a polypeptide being produced and a stable link with the mRNA encoding that polypeptide (by the action of mild UV irradiation). FIG. 2 is a schematic representation of one embodiment of the present invention. It represents steps which occur during in vitro translation that link the growing polypeptide to the tRNA analogue (top panel) and that link the tRNA analogue to the mRNA (bottom panel). As illustrated (top panel), a normal polypeptidyl containing tRNA is located in the P site and a tRNA analogue (e.g., PHE-N-tRNA in which 3'-amino-3'-deoxyadenosine is boxed), is located in the A site of a ribosome. Peptidyl transfer (represented by small arrows in the top panel) occurs, resulting in formation of a polypeptide-tRNA fusion by transfer of the peptide being produced to the amino acid moiety of the tRNA analogue (the amide link between the amino-acid moiety and the RNA portion of the tRNA analogue is shown as a very thick line). This amide link stalls protein synthesis, presumably after translocation of the polypeptide-tRNA analogue from the A site to the P site (bottom panel). Exposure of the stalled complexes to UV irradiation results in crosslinking of the polypeptide-tRNA analogue to the mRNA through the Y base of the tRNA analogue, thus generating the desired polypeptide-tRNA analogue-mRNA fusion.

The present invention also relates to the encoded polypeptides (polypeptide-tRNA analogue-mRNA fusions) which comprise the diverse libraries or collections; methods of generating or producing the diverse libraries; a method of identifying and, optionally, amplifying members of the encoded polypeptide library (referred to as target members) which have desired characteristics; target members of the library identified by the method and fragments of the target members (e.g., polypeptides, fragments of polypeptides, or fragments of polypeptide-tRNA analogue-mRNA fusions.)

In the method of generating libraries of encoded polypeptides (diverse collections of polypeptide-tRNA analogue-mRNA fusions), mRNA, tRNA analogues (e.g., PHE-N-tRNA) and an appropriate in vitro translation mixture (e.g., bacterial translation mixtures, such as from *E. coli*; eucaryotic translation mixtures, such as mixtures from wheat germ and rabbit reticulocytes, or translation mixtures from other organisms) are combined to produce a combination. The resulting combination is maintained under conditions appropriate for translation of the mRNAs, formation of stable peptide-tRNA analogue fusions (linkage between the terminal amino acid residue of the polypeptide being expressed and the stably linked amino-acid moiety, e.g., the phenylalanine of PHE-N-tRNA), and formation of a covalent linkage fusing the tRNA analogue with the mRNA. The in vitro translation mixture is a combination of biological reagents and cellular components which translate mRNAs to produce the polypeptides they encode. If the tRNA portion of the tRNA analogue is yeast tRNA$^{phe}$ then crosslinking is effected by subjecting the ribosome-bound, stalled polypeptide-tRNA-mRNA complex to UV irradiation.

Once a diverse encoded polypeptide library has been produced, it can be screened, using known methods, to identify target members which are fusions with desired characteristics. A key advantage of the encoded polypeptide library of the present invention, which is comprised of polypeptide-tRNA analogue-mRNA fusions, is that even members which occur in small numbers (rare members) and are of interest because of desired biological or biochemical properties (e.g., binding to a particular ligand, enzymatic activity) can be enriched and then identified by amplification, cloning and sequencing of their respective mRNAs.

A diverse library of encoded polypeptides can be enriched in molecules with the desired properties using known methods, to identify target members. Methods by which target members of the library can be enriched include affinity enrichment using immobilized ligand or binding partner and, for enzymatic activity, affinity to a product of a reaction in which the enzyme has modified itself (with, for example, a mechanism-based inhibitor) or a substrate to which it is attached (e.g., Williams, K. P. and D. P. Bartel, "In Vitro Selection of Catalytic RNA", pp. 367–381 In: Catalytic RNA, (Fritz Eckstein and David M. J. Lilley, Ed.), Springer, (1996)).

Furthermore, libraries enriched in target members can be amplified and subjected to additional enrichment. For example, a library of fusions that has been enriched for a desired activity (an enriched encoded polypeptide library) can be reverse transcribed, producing the cDNAs of the mRNA components. The cDNAs can then be amplified (e.g., by PCR or other amplification methods). The resulting PCR products are subjected to in vitro transcription, resulting in production of an amplified pool of mRNAs that encode the members of the enriched fusion library. In vitro translation of this pool in the presence of the tRNA analogue links the mRNAs to their translation products, producing an amplified version of the enriched encoded polypeptide library. Fusions amplified in this way are subjected to further enrichment and amplification, which is repeated as necessary until target members are enriched to the desired extent (e.g., enriched to a level where they are present in sufficient numbers to be detected by binding to a ligand of interest or catalyzing a reaction of interest). After sufficient enrichment, mRNAs of target members are cloned and individual fusions can be screened for the desired function. The translation product of the mRNA or a fragment of the translation product can also be screened for activity without attachment to the mRNA.

The method of the present invention of identifying members of a diverse library of encoded polypeptides which exhibit a desired activity is carried out as follows: A diverse library, whose members are polypeptide-tRNA anlogue-mRNA fusions, is produced by combining: 1) mRNAs which encode polypeptides; 2) tRNA analogues, which each comprise: a) a tRNA; b) an amino acid moiety which can act as an acceptor substrate, but not as a donor substrate, for ribosome-directed peptidyl transfer and c) a reactive or activatible moiety near or within the anticodon stem-loop that can mediate (mediates) the covalent coupling of the tRNA analogue to mRNA; and 3) an appropriate in vitro translation mixture, thereby producing a combination. The resulting combination is maintained under conditions appropriate for translation of the mRNAs to produce the encoded polypeptides and formation of a stable amino acid-tRNA analogue bond between the terminal amino acid residue of a polypeptide produced and the amino acid moiety present in the tRNA analogue, to form polypeptide-tRNA analogue fusions, thereby producing a mixture which contains stalled ribosomes that contain polypeptide-tRNA analogue fusions. The mixture which contains stalled ribosomes that contain the fusions is exposed to conditions which favor the crosslinking the tRNA analogue and the mRNA which encodes the polypeptide of the polypeptide-tRNA analogue fusion. As a result, polypeptide-tRNA analogue-mRNA fusions are produced, thereby producing a diverse library of encoded polypeptides. The diverse library of encoded polypeptides is enriched for members which exhibit a desired activity, thereby producing an enriched diverse library comprised of polypeptide-tRNA analogue-mRNA fusions. The resulting enriched diverse library is amplified by: reverse transcribing the mRNA components of the fusions, thereby producing the corresponding cDNA; amplifying and transcribing in vitro the corresponding cDNA, thereby producing a pool of amplified, enriched mRNA from the corresponding cDNA; combining the pool of amplified, enriched mRNA with an appropriate in vitro translation mixture and tRNA analogues (as described above), thereby producing a combination; maintaining the combination under conditions appropriate for translation of the mRNA to produce the encoded polypeptides and formation of a stable amino acid-tRNA analogue bond between the terminal amino acid residue of a polypeptide produced and the amino acid moiety present in the tRNA analogue, to form polypeptide-tRNA analogue fusions, thereby producing an amplified enriched mixture which contains stalled ribosomes that contain polypeptide-tRNA analogue fusion; and exposing the amplified enriched mixture which contains stalled ribosomes that contain polypeptide-tRNA analogue fusions to conditions which favor crosslinking of the tRNA analogue and the mRNA which encodes the polypeptide of the polypeptide-tRNA analogue fusion. The steps of enriching the diverse library and amplifying the enriched diverse library are repeated, as necessary, until members which exhibit the desired activity are present in sufficient number to be detected. Subsequently, members which exhibit the desired activity are detected. As a result, members of the diverse library which exhibit the desired activity are identified.

The translation products of the enriched mRNA (the polypeptide component of the target members), such as polypeptides which display activities of interest (e.g., ligand binding or catalytic activity), as well as engineered derivatives of these translation products which display activities of interest, are referred to as target polypeptide fragments. These target polypeptide fragments are also the subject of this invention. Target polypeptide fragments can be released or separated from target members in which they occur, using known methods (e.g., enzymes which cleave RNA), or they can be synthesized without attachment to the mRNA (e.g., using chemical synthesis or mRNA translation in the absence of the tRNA analogue. They can be used, for example, as diagnostic or therapeutic reagents (e.g., single-chain monoclonal antibodies), protein catalysts, members of binding pairs, receptors or their ligands, enzymes or enzyme substrates. Once a polypeptide fragment which has desired characteristics has been identified, it can be produced using known methods (e.g., production in an appropriate expression system, chemical synthesis).

Ribonucleoprotein fragments of the target members are also the subject of this invention. They can be used, for example, as enzymes or ligands.

The present invention is illustrated by the following examples, which are not intended to be limiting in any way.

EXAMPLES

Example 1

Crosslinking of Yeast tRNAphe and Peptidyl Analogues
Yeast tRNAphe to mRNA
Ribosome Preparation Tight couple ribosomes were prepared from *Escherichia (E.)coli* strain MRE 600. Two liters of LB broth were inoculated with 20 ml of a fresh overnight culture and incubated at 37° C. with vigorous agitation until an absorbance of 0.6 (550 nm) was reached. Culture flasks were then transferred to an ice water bath and incubated for 30 minutes. Cells were pelleted by centrifugation at 8000 rpm in a Sorvall GSA rotor, for 10 minutes, at 4° C. Cells were washed by resuspension in approximately 50 ml of buffer A (50 mM Tris-HCl, pH 7.5; 10 mM $MgCl_2$; 100 mM $NH_4Cl$, 6 mM 2-mercaptoethanol, 0.5 mM EDTA) and pelleted by centrifugation for 5 minutes at 8000 rpm in a Sorvall SS-34 rotor. The pelleted cells were then transferred to a large mortar at 4° C. Lysis of cells was performed in the 4° C. cold room by slow addition of 4° C. alumina (2.5 grams for every gram of cells) while grinding with a pestle. Typically, lysis took about twenty minutes. When lysis was complete, buffer A was added to dilute the grinding mixture to a total volume of about 30 ml. This was divided evenly between two Sorval SS-34 centrifuge tubes and the alumina was cleared from the solution by centrifugation for 5 minutes at 5000 rpm. The supernatant (cell lysate) was removed and clarified from cellular debris by centrifugation for 20 minutes at 15,000 rpm in a Sorvall SS-34 rotor; the clarification was then repeated. The $NH_4Cl$ concentration of the clarified supernatant was adjusted to 500 mM and the ribosomes were pelleted by centrifugation for 4 hours, at 4° C., at 40,000 rpm in a Beckman Ti60 rotor. The ribosome pellet was washed with approximately 5 ml of buffer B (50 mM Tris-HCl, pH 7.5; 6 mM $MgCl_2$; 100 mM $NH_4Cl$, 6 mM 2-mercaptoethanol, 0.5 mM EDTA) and then resuspended in 4 ml of buffer B by adding a small stir bar directly to the centrifuge tube and mounting the tube above a stir plate in the 4° C. coldroom. (It is important to maintain gentle stirring throughout resuspension of the ribosomes.) When the ribosomes were completely resuspended (20–60 minutes) 1 ml aliquots were layered onto 36 ml, 10–50% sucrose gradients (in buffer B) and centrifuged for 13 hours, at 4° C., at 20,000 rpm in a Beckman SW28 rotor. The gradients were fractionated and the 70S ribosome peak was collected. The magnesium concentration was adjusted to 10 mM and the ribosomes were pelleted from solution by centrifugation for 4 hours, at 4° C., at 60,000 rpm in a Beckman Ti60 rotor. The ribosome pellet was washed with 5 ml of buffer C (50 mM Tris-HCl, pH 7.5; 6 mM $MgCl_2$; 100 mM $NH_4Cl$, 0.5 mM EDTA) and resuspended as before in 1 ml of buffer C. The concentration of the ribosomes was determined at 260 nm (1 O.D. of 70S ribosomes=23 pmol) and buffer C was added to obtain a final concentration of 10 $\mu M$. The ribosomes were then aliquoted (10 $\mu l$), frozen in liquid nitrogen and stored at −70° C.

Preparation of S100 Extract

Twenty grams of *E. coli* cells were lysed and the cellular debris removed as described above. Ribosomes were removed from the clarified cell lysate by centrifugation for 4 hours, at 4° C., at 40,000 rpm in a Beckman Ti60 rotor and the supernatant was diluted two fold with buffer D (10 mM Tris-HCl pH 7.5; 30 mM $NH_4Cl$; 10 mM $MgCl_2$; and 6 mM 2-mercaptoethanol). This solution was stirred with 12 g of dry DEAE-cellulose that was equilibrated with buffer D, washed with distilled water, and then dried. The slurry was filtered on a scintered glass funnel and washed with 1–2 liters of buffer D. The DEAE-cellulose cake was resuspended in buffer D and packed in a column. The S100 extract was then eluted with buffer D containing 250 mM $NH_4Cl$ (the desired fractions elute as a sharp band and can usually be identified by eye as they have a pale yellow color. Small aliquots (100 $\mu l$) of the purified S100 extract were frozen in liquid nitrogen and stored at −70 ° C. The tRNA charging efficiency of S100 was determined by monitoring TCA-precipitable counts in the presence of $tRNA^{phe}$ and radiolabeled phenylalanine [S100 is incubated for 10 minutes at 37° C. with $tRNA^{phe}$ (1 $\mu M$), 14C-phenylalanine (20 $\mu M$), and ATP (2 mM) in 30 mM Tris-HCl pH 7.5, 15 mM 1M $MgCl_2$, 25 mM KCl, 4 mM DTT].

Preparation of tRNAs and mRNA

Yeast $tRNA^{phe}$ was purchased from Sigma. Elongator methionine tRNA was transcribed by T7 polymerase from DNA obtained by PCR amplification of *E. coli* chromosomal DNA using the (+) strand primer TAA-TAC-GAC-TCA-CTA-TAG-GCT-ACG-TAG-CTC-AGT-TGG (SEQ ID NO.: 1) and the (−) strand primer TGG-TGG-CTA-CGA-CGG-GAT-TC (SEQ ID NO.: 2). A portion of the T4 gene-32 mRNA was transcribed by T7 polymerase from a PCR amplified section (−55 to +85) of plasmid pKsK12A (Krisch and Allet, *PNAS* (*USA*), 79:4937–4941 (1982)) using the (+) strand primer TAA-TAC-GAC-TCA-CTA-TAG-GTA-AAG-TGT-CAT-TAG-C (SEQ ID NO.: 3) and the (−) strand primer CTT-TAT-CTT-CAG-AAG-AAA-AAC-C (SEQ ID NO.: 4). The mRNA was labeled with yeast polyA polymerase and $^{32}P$ labeled cordycepin.

Amino Acylation and Acetylation of Yeast tRNAphe

Amino acylation of yeast $tRNA^{phe}$ (1 $\mu M$) with phenylalanine (20 $\mu M$) was performed by incubation for 10 minutes at 37° C. with ATP (2 mM) and the appropriate amount of S100 in 30 mM Tris-HCl pH 7.5, 15 mM 1M MgCl2, 25 mM KCl, 4 mM DTT. To stop the reaction and recover the acylated tRNA (PHE-$tRNA^{phe}$; typically 70% yield) one-tenth volume of 3M NaOAc pH 5.0 was added, and the reaction was extracted two times with acid phenol, two times with chloroform, and precipitated with 2.5 volumes of ethanol. The PHE-$tRNA^{phe}$ was resuspended at a concentration of 10 $\mu M$ in 0.2M NaOAc pH 5.0 and the amine of the phenylalanine was acetylated (to produce the peptidyl analogue N-acetyl-PHE-$tRNA^{phe}$) by adding one-hundredth volume of acetic anhydride followed by incubation on ice for 30 minutes. A fresh aliquot of acetic anhydride was added and the incubation continued for another 30 minutes. The reaction was stopped and the N-acetyl-PHE-$tRNA^{phe}$) isolated by adding 2.5 volumes of ethanol and precipitating. N-acetyl-PHE-tRNAphe was resuspended at a concentration of 10 $\mu M$ in 10 mM NaOAc pH 5.0 and stored at −20° C.

Binding of mRNA and tRNA to the Ribosome and Crosslinking of N-acetyl-PHE-tRNAphe to the mRNA Ribosomal complexes with $tRNA^{met}$ bound to the P site of the ribosome and the first codon (AUG) of the labeled gene-32 mRNA were formed by incubating ribosomes (0.5 $\mu M$), $tRNA^{met}$ (1 $\mu M$), and mRNA (5 $\mu M$) in 25 $\mu l$ of buffer (Tris-HCl ph 7.5, 30 mM $NH_4Cl$, 20 mM $MgCl_2$) for 10 minutes at 37° C. Deacylated yeast $tRNA^{phe}$ was bound to the A site (corresponding to the second codon (UUU) of the mRNA) by adding 25 pmol of the tRNA and continuing the incubation for an additional 10 minutes. Alternatively, N-acetyl-PHE-$tRNA^{phe}$ was bound to the P site by adding 25 pmol of N-acetyl-PHE-$tRNA^{phe}$ and continuing the incubation for an additional 10 minutes; the tRNA initially binds to the A site but spontaneous translocation should move it into the P site of the ribosome. The phenylalanine tRNA in either type of complex was crosslinked to the mRNA by spotting the reaction on a petri dish and irradiating for 45 minutes (at a distance of 10 cm) with a 450 watt, medium pressure, mercury vapor lamp (ACE glass). The samples were maintained at 4° C. during the irradiation and short wavelength UV light was blocked by a suitable filter (the top of a plastic petri dish). The extent of crosslinking between the mRNA and tRNA (typically ~20% of the ribosomes contain crosslinked, tRNA-mRNA fusions) was determined by polyacrylamide gel electrophoresis.

Example 2
Synthesis of a Bifunctional tRNA and its Use in Generating Encoded Peptide Libraries
PHE-N-tRNA A method to produce PHE-N-tRNA involves replacement of the 3'-terminal A of a tRNA with 3'-amino-3'-deoxyadenosine and charging of the 3'-amino-3'-deoxyadenosine substituted tRNA with phenylalanine (Fraser, T. H. and Rich, A., *Proc. Nat. Acad. Sci. USA* 70:2671 (1972)). Using this procedure with yeast tRNA$^{phe}$ generates PHE-N-tRNA, a tRNA analogue that can act as an acceptor substrate but not a donor substrate during protein synthesis and that can be crosslinked to mRNA. First, the 3'-terminal A, of yeast tRNA$^{phe}$ is removed (resulting in tRNA(-A)) and then 3'-amino-3'-deoxyadenosine monophosphate is attached to the end of tRNA(-A) by the action of tRNA nucleotidyl transferase. This 3'-amino-3'-deoxyadenosine substituted tRNA is then charged with phenylalanine and S100.

Strategy for Synthesis of a Bifunctional tRNA (PURO-tRNA$^{phe}$)

A method to produce PURO-tRNA (a tRNA with its 3' terminal A residue replaced by puromycin) involves replacement of the 3'-terminal C and A of a tRNA with pCpPuromycin (puromycin that has been extended at its 5' hydroxyl by a 3', 5-cytidine diphosphate). The 3'-terminal C and A of yeast tRNAphe are removed (resulting in tRNA(-CA)) and then pCpPuromycin is ligated to the end of the truncated tRNA to seamlessly fuse the two molecules. Using this procedure with yeast tRNA$^{phe}$ generates PURO-tRNA$^{phe}$, a tRNA analogue that can act as an acceptor substrate but not a donor substrate during protein synthesis and that can be crosslinked to mRNA.

Removal of the 3'-Terminal A and Removal of the 3'-Terminal C and A of Yeast tRNA$^{phe}$ Yeast tRNA$^{phe}$ (300 μM) and venom phosphodiesterase (*Crotalus atrox*) were incubated in 40 mM glycine-NaOH pH 8.7, and 10 mM magnesium acetate for 10 minutes at 37° C. Typically, 0.1 to 10 mg of venom per ml have been used in the literature; however, it was useful to titrate the venom to identify the concentration that produced quantitative removal of the C and A. After incubation, the reaction was brought to 0.3 M sodium acetate, 5 mM EDTA, 0.5% SDS, phenol extracted three times, chloroform extracted two times, 2.5 volumes of ethanol were added and the tRNA was precipitated. If tRNA(-A) was the desired product the tRNA was incubated with tRNA nucleotidyl transferase and CTP in 50 mM Glycine pH 9.2, 30 mM KCl 12.5 mM MgCl$_2$, 2.5 mg/ml reduced glutathione and 0.375 mg/ml BSA for 30 minutes. The reaction was phenol extracted and tRNA(-A) resuspended in water. If the desired product was tRNA(-CA) the tRNA was purified by polyacrylamide gel electrophoresis and was resuspended in water and then adjusted to a concentration of 10 μM in 70 mM Tris-HCl pH 8.5, 30 mM MgCl2, and 1.6 mM DTT.

Synthesis of 3'-amino-3'-deoxyadenosine and Attachment to tRNA(-A).

3'-amino-3'-deoxyadenosine was made by the method of Gerber and Lechevalier (*J. Org. Chem.* 27:1731(1962)) and can be phosphorylated according to Fraser and Rich (*Proc. Nat. Acad. Sci. USA* 70:2671 (1973)). 3'-amino-3'-deoxyadenosine triphosphate, tRNA(-A), and tRNA nucleotidyl transferase were used to generate yeast N-tRNA (yeast tRNA$^{phe}$ whose 3'-terminal adenosine has been substituted with 3'-amino-3'-deoxyadenosine) by incubation at 37° C. for 30 minutes in 50 mM Glycine pH 9.2, 30 mM KCl, 12.5 mM MgCl$_2$, 2.5 mg/ml reduced glutathione and 0.375 mg/ml BSA. PHE-N-tRNA was generated by incubating N-tRNA, phenylalanine and S100 at 37° C. for 30 minutes in 30 mM Tris pH 7.5, 25 mM KCl, 15 mM MgCl$_2$, and 4 mM DTT. PHE-N-tRNA was purified by HPLC.

Synthesis of pCpPuromycin and Attachment to the Truncated tRNA

Several methods have been used to make CpPuromycin and CpPuromycin analogues (e.g. Harris, R. J. et al., *Can. J. Bioch.*, 50:918–926(1972); Nyilas, A. et al., *Bioorganic and Medicinal Chemistry Letters*, 3(6):1371–1374(1993); Green and Noller, *Science*, 1998). CpPuromycin prepared by the method of Green and Noller (1998) is used. CpPuromycin (10 μM) is phosphorylated by incubation at 37° C. for 30 minutes with T4 polynucleotide kinase in 70 mM Tris-HCl pH 7.5, 10 mM MgCl2, 5 mM DTT, and 30 μM ATP. (It is important to keep the concentration of ATP at 2–5 fold over the concentration of CpPuromycin as the subsequent ligation is sensitive to excessive ATP). The kinase is inactivated by heating the reaction to 65 ° C. for 20 minutes. The solution is brought to 20 μg/ml BSA, an equal volume of 10 μm tRNA(-CA) in (70 mM Tris-HCl pH 8.5, 50 mM MgCl2, and 1.6 mM DTT) is added, and the solution is incubated for 60 minutes at 37° C. with T4 RNA ligase. Ligation of pCpPuromycin to tRNA(-CA) produces the desired PURO-tRNA$^{phe}$ product which is purified by polyacrylamide gel electrophoresis.

Example 3
Using the bifunctional tRNA to generate an encoded polypeptide library An in vitro translation mixture is combined with a complex pool of mRNA sequences, and an appropriate amount of a bifunctional tRNA (PHE-N-tRNA or PURO-tRNA$^{phe}$). The translation mixture contains all of the factors required for in vitro translation (e.g., initiation factors, the tRNAs, elongation factors, amino acids, etc.) except for mRNA. Translation mixtures are purchased (Promega) or they can be made from crude cellular extracts (extracts from several organisms are used and protocols for making them are readily available in the literature). The appropriate concentration of a bifuntional tRNA is added to the translation mixture. Translation is initiated by the addition of the complex pool of mRNA sequences. All of the members of the pool of mRNA sequences have a constant sequence at their 5' end that permits them to be translated by the ribosome, an internal, randomized, polypeptide-coding segment that is devoid of stop codons, and a UUU- and UUC-rich 3' coding segment that recruits a bifunctional tRNA after translation of the randomized segment is completed. The bifunctional tRNA concentration in the translation mixture is carefully adjusted so that during translation, the UUU and UUC codons that are contained within the randomized coding segment are decoded by normal phenylalanine tRNA that are present in the translation mixture. When the UUU- and UUC-rich 3' coding segment (of each translating mRNA) is reached, there is a high probability that a bifunctional tRNA will eventually be selected to decode a UUU or UUC codon. Decoding by a bifunctional tRNA stalls translation of the mRNA because a bifunctional tRNA can accept the growing polypeptide chain but cannot transfer the polypeptide chain to another acylated tRNA. This generates polypeptide-bifunctional tRNA fusions that are bound to ribosomes. The translation mixture is concurrently or subsequently irradiated at a distance of 10 cm with a 450 watt, medium pressure, mercury vapor lamp (ACE glass; short wavelength UV light is blocked by a suitable filter). This activates the Y base of the bifunctional tRNA and causes the base (and therefore the polypeptide-bifunctional tRNA fusion) to become crosslinked to the mRNA that encodes the polypeptide. After irradiation, disruption of the ribosomes with EDTA releases the encoded polypeptide library so that it can be purified and used.

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A polypeptide-tRNA analogue-mRNA fusion, comprising:
   (a) a polypeptide;
   (b) a tRNA analogue comprising:
      (i) an amino acid moiety linked to the tRNA wherein the link is modified structurally so that the amino acid moiety acts as an acceptor substrate, but not as a donor substrate, for ribosome-directed peptidyl transfer, wherein the amino acid moiety is at the 3' end of the tRNA; and
      (ii) ac activatible moiety near or within the anticodon stem-loop that can become reactive and thereby mediate the specific, stable coupling of the tRNA analogue to mRNA; and
   (c) mRNA which encodes the polypeptide of (a),
   wherein the tRNA analogue is: located between the polypeptide and the mRNA; linked to the carboxy terminus of the polypeptide by a covalent bond between the terminal amino acid residue of the polypeptide and the amino acid moiety and, linked to the mRNA by covalent bonds between the reactive moiety of the tRNA analogue and the mRNA.

2. The polypeptide-tRNA analogue-mRNA fusion of claim 1, wherein the tRNA analogue is a 3'-amino-3'-deoxyadenosine-substituted tRNA or puromycin-substituted tRNA and the amino acid moiety is any amino acid or the methoxytyrosine moiety of puromycin.

3. The polypeptide-tRNA analogue-mRNA fusion of claim 1, wherein the tRNA is yeast tRNA$^{phe}$.

4. The fusion of claim 3, wherein the tRNA is yeast tRNA$^{phe}$ in which the 3' terminal nucleotide has been replaced by 3'-amino-3'-deoxyadenosine or puromycin.

5. A polypeptide-tRNA analogue-mRNA fusion, comprising:
   (a) a polypeptide;
   (b) a tRNA analogue comprising:
      (i) an amino acid moiety linked to the tRNA wherein the link is modified structurally so that the amino acid moiety acts as an acceptor substrate, but not as a donor substrate, for ribosome-directed peptidyl transfer, wherein the amino acid moiety is at the 3' end of the tRNA; and
      (ii) an activatible moiety near or within the anticodon stem-loop that can become reactive and thereby mediate the specific, stable coupling of the tRNA analogue to mRNA; and
   (c) mRNA which encodes the polypeptide of (a),
wherein the tRNA analogue is: located between the polypeptide and the mRNA; linked to the polypeptide by a covalent bond between the terminal amino acid residue of the carboxy terminus of the polypeptide and the amino acid moiety; and linked to the mRNA by the action of UV irradiation that produces a covalent bond between a modified base near or within the tRNA stem loop and the mRNA.

6. The fusion of claim 5, wherein the tRNA analogue is a 3'-amino-3'-deoxyadenosine-substituted tRNA or puromycin-substituted tRNA and the amino acid moiety is any amino acid or the methoxytyrosine moiety of puromycin-substituted tRNA.

7. The fusion of claim 5, wherein the tRNA is yeast tRNA$^{phe}$ in which the 3' terminal nucleotide has been replaced by 3'-amino-3'-deoxyadenosine or puromycin.

8. A polypeptide-tRNA analogue-mRNA fusion, comprising:
   (a) a polypeptide;
   (b) a tRNA analogue comprising:
      (i) an amino acid moiety linked to the tRNA wherein the link is modified structurally so that the amino acid moiety acts as an acceptor substrate, but not as a donor substrate, for ribosome-directed peptidyl transfer, wherein the amino acid moiety is at the 3' end of the tRNA; and
      (ii) an activatible Y base within the anticodon stem-loop that can become reactive and thereby mediate the specific, stable coupling of the tRNA analogue to mRNA; and
   mRNA which encodes the polypeptide of (a),
wherein the tRNA analogue is: located between the polypeptide and the mRNA; linked to the carboxy terminus of the polypeptide by a covalent bond between the terminal amino acid residue of the polypeptide and the amino acid moiety and, linked to the mRNA by covalent bonds between the Y-base of the tRNA analogue and the mRNA.

9. The polypeptide-tRNA analogue-mRNA fusion of claim 8, wherein the tRNA analogue is a 3'-amino-3'-deoxyadenosine-substituted tRNA or puromycin-substituted tRNA and the amino acid moiety is any amino acid or the methoxytyrosine moiety of puromycin.

10. The polypeptide-tRNA analogue-mRNA fusion of claim 8, wherein the tRNA is yeast tRNA.

11. The fusion of claim 10, wherein the tRNA is yeast tRNA$^{phe}$ in which the 3' terminal nucleotide has been replaced by 3'-amino-3'-deoxyadenosine or puromycin.

* * * * *

UNITED STATES PATENT AND TRADEMARK OFFICE
CERTIFICATE OF CORRECTION

PATENT NO. : 6,440,695 B1
DATED : August 27, 2002
INVENTOR(S) : Charles Everett Merryman and David P. Bartel It is certified that error appears in the above-identified patent and that said Letters Patent is hereby corrected as shown below:

Column 16,
Line 18, before "mRNA", insert -- (c) --;
Line 31, replace "yeast tRNA" with -- yeast tRNA$^{phe}$. --

Signed and Sealed this

Twenty-eighth Day of January, 2003

JAMES E. ROGAN
*Director of the United States Patent and Trademark Office*